(12) United States Patent
Shade et al.

(10) Patent No.: US 7,285,419 B2
(45) Date of Patent: Oct. 23, 2007

(54) ANALYSIS OF MERCURY CONTAINING SAMPLES

(75) Inventors: Christopher W. Shade, Champaign, IL (US); Robert J. M. Hudson, Champaign, IL (US)

(73) Assignee: The Board of Trustees of the University of Illinois, Urbana, IL (US)

( * ) Notice: Subject to any disclaimer, the term of this patent is extended or adjusted under 35 U.S.C. 154(b) by 577 days.

(21) Appl. No.: 10/171,461

(22) Filed: Jun. 11, 2002

(65) Prior Publication Data

US 2003/0228699 A1     Dec. 11, 2003

(51) Int. Cl.
    *G01N 33/00*     (2006.01)
(52) U.S. Cl. .......................... 436/81; 436/73; 436/180; 436/174
(58) Field of Classification Search ............... 422/68.1, 422/69, 81, 82.09; 436/73, 81, 180, 174
    See application file for complete search history.

(56) References Cited

U.S. PATENT DOCUMENTS

| | | | | |
|---|---|---|---|---|
| 4,038,071 A | * | 7/1977 | Di Bella | 588/319 |
| 4,160,730 A | * | 7/1979 | Nguyen | 210/718 |
| 5,026,652 A | | 6/1991 | Huber | |
| 5,459,040 A | | 10/1995 | Hammock et al. | |

FOREIGN PATENT DOCUMENTS

| | | |
|---|---|---|
| DE | 100 11 171 A1 | 9/2001 |
| EP | 0 402 696 A1 | 12/1990 |

OTHER PUBLICATIONS

Castro, Total Mercury Concentrations in Lakes and Fish of Western Maryland, May 2002, Springer New York, ISSN 0090-4341 (Print) 1432-0703 (online), vol. 42, No. 4/ May 2002, pp. 454-462.*

Bagheri, H. et al., "Determination of Very Low Levels of Dissolved Marcury(II) and Methylmercury in River Waters by Continuous Flow with On-Line UV Decomposition and Cold-Vapour Atomic Fluorescence Spectrometry After Pre-Concentrations on a Silica Gel-2-Mercaptobenzimidazol Sorbent", *Talanta*, vol. 55, 2001, pp. 1141-1150.

Bloom, N. et al., "Determination of Volatile Mercury Species at the Picogram Level by Low-Temperature Gas Chromatography with Cold-Vapour Atomic Fluorescence Detection", *Analytica Chimica Acta*, vol. 208, 1988, pp. 151-161.

"Catalogue of the Manufacturers and Suppliers of Instrumentation Equipment and Laboratory Equipment", http://www.spectrometer.ru/manufacturers-suppliers/mercury-analyzers.htm, 2000, printed on Feb. 20, 2002, pp. 1-5.

(Continued)

*Primary Examiner*—Jill Warden
*Assistant Examiner*—Samuel P Siefke
(74) *Attorney, Agent, or Firm*—Evan Law Group LLC

(57) ABSTRACT

Methods of analyzing mercury containing samples for inorganic and organomercurial complexes are disclosed. The methods are highly sensitive and are especially suited to samples containing significant amounts of organic matter. Kits and devices for mercury analysis are also disclosed.

51 Claims, 4 Drawing Sheets

OTHER PUBLICATIONS

Costa-Fernandez, J. et al., "Direct Coupling of High-Performance Liquid Chromatography to Microwave-induced Plasma Atomic Emission Spectrometry via Volatile-species Generation and Its Application to Mercury and Arsenic Speciation", *Journal of Analytical Atomic Spectrometry*, vol. 10, 1995, pp. 1019-1025.

Eiden, R. et al., "Distillation, On-Line RP C18 Preconcentration and HPLC-UV-PCO-CVAAS as a New Combination for the Determination of Methylmercury in Sediments and Fish Tissue", *Fresenius J Anal Chem*, vol. 357, 1997, pp. 439-441.

Emteborg, H. et al., "Speciation of Mercury in Natural Waters by Capillary Gas Chromatography with a Microwave-Induced Plasma Emission Detector Following a Preconcentration Using a Dithiocarbamate Resin Microcolumn Installed in a Closed Flow Injection System", *Analyst*, vol. 118, 1993, pp. 1007-1013.

Falter, R. et al., "Coupling of the RP C18 Preconcentration HPLC-UV-PCO-System with Atomic Fluorescence Detection for the Determination of Methylmercury in Sediment and Biological Tissue", *Fresenius J Anal Chem*, vol. 358, 1997, pp. 407-410.

Falter, R. et al., "Determination of Dimethyl- and Diethylmercury with HPLC-CVAAS by On-Line UV-irradiation", *Fresenius J. Anal Chem*, vol. 348, 1994, pp. 253-254.

Falter, R. et al., "Determination of Mercury Species in Natural Waters at Picogram Level with On-Line RP C18 Preconcentration and HPLC-UV-PCO-CVAAS", *Fresenius J Anal Chem*, vol. 353, 1995, pp. 34-38.

Falter, R. et al., "Interfacing High-Performance Liquid Chromatography and Cold-Vapour Atomic Absorption Spectrometry with On-Line UV Irradiation for the Determination of Organic Mercury Compounds", *Journal of Chromatography A*, vol. 675, 1994, pp. 253-256.

Horvat, M. et al., "Comparison of Distillation with Other Current Isolation Methods for the Determination of Methyl Mercury Compounds in Low Level Environmental Samples", *Analytica Chimica Acta*, vol. 282, 1993, pp. 153-168.

Liu, P. et al. "Synthesis of Silica Gel Immobilized Thiourea and its Application to the On-Line Preconcentration and Separation of Silver, Gold and Palladium", *Analyst*, vol. 125, 2000, pp. 147-150.

Ma, W. et al., "Preconcentration, Separation and Determination of Trace Hg(II) in Environmental Samples with Aminopropylbenzoylazo-2-Mercaptobenzothiazole Bonded to Silica Gel", *Analytica Chimica Acta*, vol. 416, 2000, pp. 191-196.

Mahmoud, M. et al., "Selective Pre-Concentration and Solid Phase Extraction of Mercury(II) from Natural Water by Silica Gel-Loaded Dithizone Phases", *Analytica Chimica Acta*, vol. 415, 2000, pp. 33-40.

Mahmoud, M., "Selective Solid Phase Extraction of Mercury(II) by Silica Gel-Immobilized-Dithiocarbamate Derivatives", *Analytica Chimica Acta*, vol. 398, 1999, pp. 297-304.

Manzoori, J. et al., "Determination of Mercury by Cold Vapour Atomic Absorption Spectrometry after Preconcentration with Dithizone Immobilized on Surfactant-Coated Alumina", *Journal of Analytical Atomic Spectrometry*, vol. 13, 1998, pp. 305-308.

"Mercury in Water by Cold Vapor Atomic Fluorescence Spectrometry", Method 245.7, *U.S. Environmental Protection Agency*, 2001, pp. 1-31.

"Mercury in Water by Oxidation, Purge and Trap, and Cold Vapor Atomic Fluorescence Spectrometry", Method 1631, Revision B., *U.S. Environmental Protection Agency*, 1999, pp. 1-14.

"Methyl Mercury in Water by Distillation, Aqueos Ethylation, Purge and Trap, and CVAFS", Method 1630, *U.S. Environmental Protection Agency*, 2001.

"M-6000A Mercury Analyzer- Uncompromising Mercury Determinations", *Varian*, Pub. No. 85 101511 00 Feb. 1996, 1996, pp. 1-6.

Pu, Q. et al., "2-Mercaptobenzothiazole-Bonded Silica Gel as Selective Adsorbent for Preconcentration of Gold, Platinum and Palladium Prior to their Simultaneous Inductively Coupled Plasma Optical Emission Spectrometric Determination", *Journal of Analytical Atomic Spectrometry*, vol. 13, 1998, pp. 249-253.

Qvarnstrom, J. et al., "Flow Injection-Liquid Chromatography-Cold Vapour Atomic Absorption Spectrometry for Rapid Determination of Methyl and Inorganic Mercury", *Analyst*, vol. 125, 2000, pp. 1193-1197.

Rio-Segade, S. et al., "On-Line High-Performance Liquid-Chromatographic Separation and Cold Vapor Atomic Absorption Spectrometric Determination of Methylmercury and Inorganic Mercury", *Talanta*, vol. 48, 1999, pp. 477-484.

Sarzanini, C. et al., "Simultaneous Determination of Methyl-, Ethyl-, Phenyl-, and Inorganic Mercury by Cold Vapour Atomic Absorption Spectrometry with On-Line Chromatographic Separation", *Journal of Chromatography*, vol. 626, 1992, pp. 151-157.

"Ultra-Trace Mercury Analysis", *Tekran Inc.*

Yin, X. et al., "Mercury Speciation by Coupling Cold Vapour Atomic Absorption Spectrometry with Flow Injection On-Line Preconcentration and Liquid Chromatographic Separation", *Fresenius J Anal Chem*, vol. 361, 1998, pp. 761-766.

Zuo, Guangju et al., "Selective binding of mercury to thiourea-based coordinating resins", *Reactive & Functional Polymers*, vol. 27, 1995, pp. 187-198.

International Search Report for Patent Cooperation Treaty application No. PCT/US03/17605, dated Oct. 7, 2003, 3 pages.

* cited by examiner

ANALYSIS OF MERCURY CONTAINING SAMPLES

FEDERALLY SPONSORED RESEARCH OR DEVELOPMENT

This application may have been funded in part under a U.S. Government grant. The U.S. Government may have rights in this invention.

BACKGROUND

Mercury pollution is of growing global concern due to the widespread atmospheric transport of gaseous mercury species and its biological toxicity. After being scavenged from the atmosphere, inorganic mercury ($Hg^{2+}$) is methylated in anoxic zones of aquatic and terrestrial ecosystems to form organomercurial compounds, including monomethylmercury. Unlike inorganic mercury, the high biological transfer efficiency of organomercurial compounds allows them to biomagnify in a similar fashion to organic compounds. Biomagnification is the ability of a species to build up to high levels in the microscopic animals, fish, and fish consumers that make up aquatic and terrestrial food webs. The significant difference between the toxicity of organomercurial compounds and inorganic mercury makes the analytical methods for distinguishing these different mercury species critical for both research and environmental monitoring purposes.

For example, in the decade since the development of the aqueous [ethylation/gas chromatography (GC)/atomic fluorescence spectrometry (AFS)] analysis method was developed, our understanding of the biochemistry of monomethylmercury has increased. This method, however, is difficult and time consuming, which limits its use. Despite the previous progress with the [ethylation/GC/AFS] method, there is a need for more rapid analytical methods to reduce the difficulty and cost of measuring monomethylmercury at environmental concentrations.

Existing high-pressure liquid chromatography (HPLC) based systems for separation and quantification of inorganic and monomethylmercury have failed to overcome the key obstacles inherent in environmental mercury analysis: trace-level detection and matrix interferents. Due to the very low, or trace-level, amounts of mercury in the environment, analytical methods must be very sensitive. Additionally, they must retain this sensitivity in the presence of matrix interferents, which are common in lakes, streams, rivers, cell cultures, experimental media, tissue digestates, and sediment extractions.

Matrix interferents include organic molecules of natural or synthetic origin. Organic molecules of natural origin include inorganic and organic byproducts of microbial metabolism, such as sulfide and thiosulfate, products of plant and animal death and decay, such as humic acid and organic acids functionalized with thiol groups, and iron oxide colloids. Interferents of synthetic origin include EDTA, NTA, amines, amino acids, and thiosulfate.

In particular, the reduced sulfur sites present in many matrix interferents form very strong bonds with mercury. This effect can prevent monomethylmercury from being directly analyzed without complex distillation or solvent extraction from water with high interferent content.

While reverse-phase HPLC methods can separate hydrophobic 2:1 and 1:1 mercury complexes formed from ligands, such as dithiocarbamates or cysteine, current preconcentration methods coupled with HPLC are not effective at the trace mercury levels present in many environmental samples. More importantly, none of these methods can analyze for both inorganic and monomethylmercury, when significant organic and/or sulfide interferents are present in the sample. The current invention overcomes at least one of the disadvantages associated with prior analysis methods.

BRIEF SUMMARY

In one aspect, a method for mercury analysis is provided that includes reducing the pH of a sample comprising mercury and matrix interferents to $pH \leq 2.5$ and adsorbing the mercury onto one or more resins at $pH \leq 2.5$. The mercury is separated into inorganic and $R-Hg^+$ species and quantified.

In aqueous solutions, mercury can exist in a wide variety of "species" or molecules distinguished by charge and composition. The broadest classes of mercury species found in aqueous solution may be termed "inorganic" or "organic," depending on whether the species contains a mercury-carbon bond.

Inorganic mercury species, which do not contain a mercury-carbon bond, are divided among three formal oxidation states: the elemental mercury ($Hg^\circ$) species, the complexes of mercurous ion ($Hg^{2+}$), and the complexes of mercuric ion ($Hg^{2+}$). Organic mercury species include a wide array of natural and synthetic compounds. These compounds may be subdivided into species with one or two mercury-carbon bonds. The species with one mercury-carbon bond ($R-Hg^+$) are monovalent cations that may form rapidly reversible coordination complexes, just as inorganic mercuric and mercurous ions.

Mercuric mercury ($Hg^{2+}$) is the main inorganic form of mercury in most fresh water bodies. This inorganic, ionic form of mercury can strongly associate with various substances, including halide ions, hydroxides, sulfides, amines, humic acids, and fulvic acids, to form coordination complexes. As defined herein, mercuric mercury is referred to as inorganic or $Hg^{2+}$.

A second form of inorganic mercury is mercurous mercury ($Hg^{(1)}$), which is in the $+1$ formal oxidation state. It is not commonly found in natural water samples, but may be found in experimental media or soils. Mercurous mercury is detected as $Hg^{2+}$ by the preferred embodiments.

The third form of inorganic mercury is elemental mercury ($Hg^\circ$), which is uncharged and volatile. Elemental mercury does not strongly associate with the molecules that complex $Hg^{2+}$ in aqueous solution. While elemental mercury does exist at measurable concentrations in water, it is normally a small portion of the total mercury present. The present invention does not detect elemental mercury ($Hg^\circ$). As further used herein, "inorganic" or $Hg^{2+}$ mercury does not include elemental mercury ($Hg^\circ$).

The second important class of mercury found in water is organic mercury species or organomercurials. While organomercurials are also in the same $+2$ formal oxidation state as inorganic mercury, the species have a mercury-carbon bond, such as a covalent bond, to an organic ligand. While the organic ligand could be methyl, ethyl, linear or branched alkyl, cycloalkyl, or aromatic, for example, the methylmercury bond is most common in nature. In freshwaters, monomethylmercury, in which a single methyl group is bonded to the mercury atom, is the most common organomercurial.

As used herein, all organomercurials with a single mercury-carbon bond are referred to as "organic" or $R-Hg^+$. These $R-Hg^+$ species can exist as monovalent cations or their coordination complexes, and may additionally associate the same ligands that bind mercuric mercury ($Hg^{2+}$).

Organomercurials with two mercury-carbon bonds are also known. The most common form found in nature is dimethylmercury, which is detectable in seawater, but not in freshwater systems. This form of mercury is volatile, uncharged, and does not form complexes with ligands that would normally associate with mercuric or monomethylmercury. As used herein, "organic" or R—$Hg^+$ mercury do not include dimethylmercury.

The present invention preferably analyzes for $Hg^{2+}$ and R—$Hg^+$ using a single process. The present invention can also analyze samples containing synthetic mercury complexes, for example when mercury is complexed with acetate, EDTA, amines, amino acids, and NTA.

In another aspect, a method for mercury analysis is provided that includes separately eluting $Hg^{2+}$ and R—$Hg^+$ species from a resin with an aqueous eluent containing protons, a bifunctional moiety, and competing cations. The $Hg^{2+}$ and R—$Hg^+$ species are then quantified.

In another aspect, a method for mercury analysis is provided that includes acidifying a sample containing $Hg^{2+}$ and R—$Hg^+$ species to a $pH \leq 2.5$ and adsorbing the mercury species from the sample at $pH \leq 2.5$ onto a resin modified with a bifunctional moiety. The $Hg^{2+}$ and R—$Hg^+$ species are then quantified.

In another aspect, a method for mercury analysis is provided that includes oxidizing R—$Hg^+$ species to $Hg^{2+}$ species, adding ascorbic acid, and reducing said $Hg^{2+}$ species to $Hg^{\circ}$ species. The $Hg^{\circ}$ species is then quantified.

In another aspect, a kit for mercury analysis is provided that includes a preconcentration column containing a resin modified with a bifunctional moiety.

In another aspect, a kit for mercury analysis is provided that includes a bifunctional moiety, enough acid to lower the pH of a sample containing mercury and matrix interferents to a $pH \leq 2.5$, and a column containing a cation exchange resin.

In another aspect, a device for mercury analysis is provided that includes a cation exchange resin that can separate $Hg^{2+}$ and R—$Hg^+$ species in the presence of an eluent. The eluent includes protons, a bifunctional moiety, and competing cations.

DETAILED DESCRIPTION

The present invention includes a novel method for separation and quantification of inorganic ($Hg^{2+}$) and organic (R—$Hg^+$) compounds. Preferred preconcentrations approach 100% efficiency, permitting separation (speciation) and quantification of very low levels of $Hg^{2+}$ and R—$Hg^+$. Separations may be performed on a column using thiourea as a mercury complexing agent. The disclosed methods are rapid, yet highly sensitive, and effective in the presence of matrix interferents, and will therefore be of interest to ecotoxicologists, biogeochemists, biochemists, and analytical chemists. The methods are suited to both laboratory and field studies of, for example, synthetic media, aquatic systems, sedimentation samples, and digested tissues, such as digested fish tissue.

Figure 1:
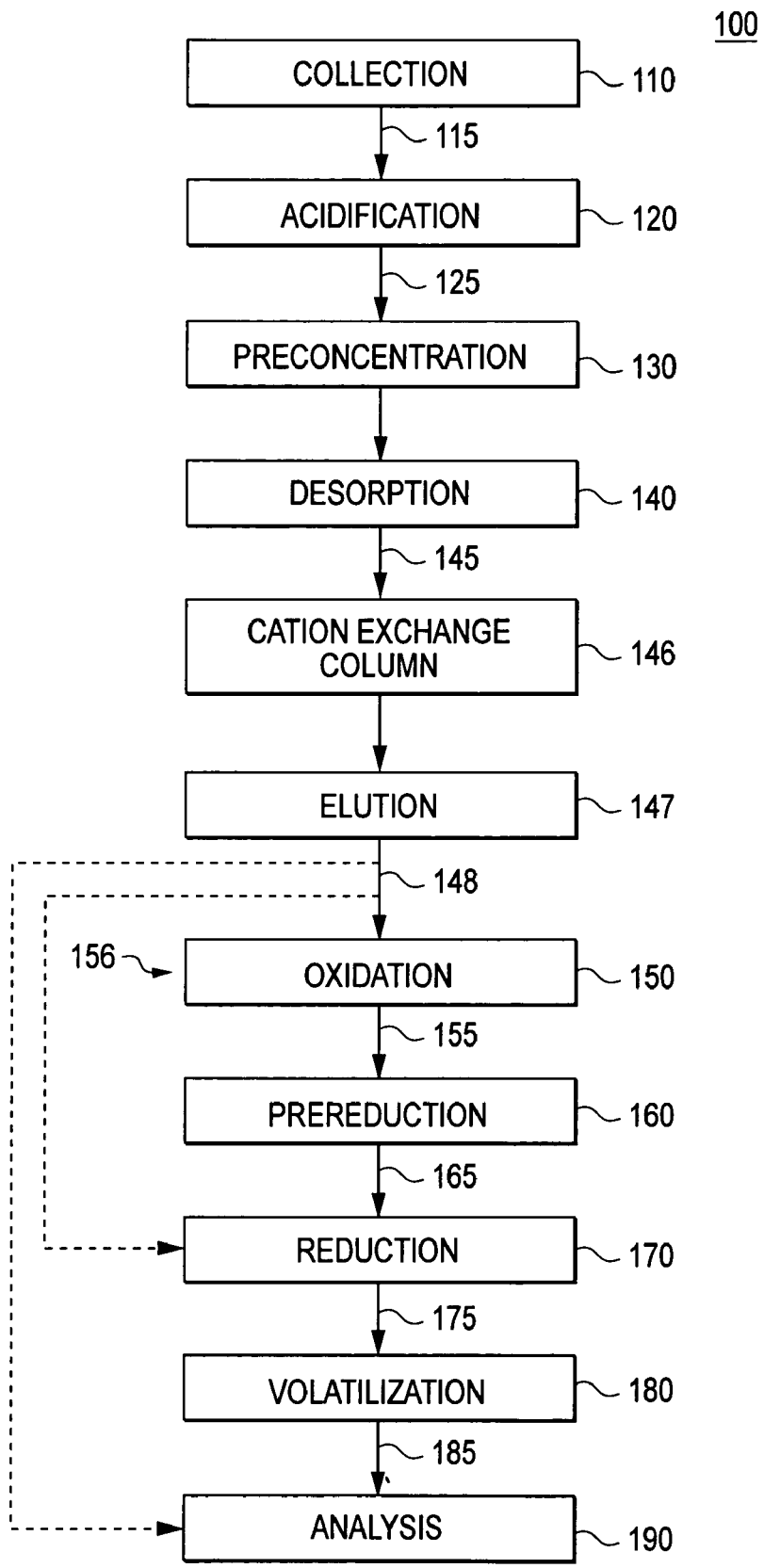
FIG. 1 depicts exemplary steps for mercury analysis by the current invention.

Referring to FIG. 1, in one embodiment, a mercury containing sample is collected during collection 110. During collection 110, the sample is optionally filtered to remove particulate matter. Collected sample 115 is then passed to acidification step 120. Acidified sample 125 is then passed to preconcentration 130. During preconcentration 130, the $Hg^{2+}$ and R—$Hg^+$ species are adsorbed onto a resin. During desorption 140, $Hg^{2+}$ and R—$Hg^+$ species are desorbed to form mercury containing solution 145.

Mercury containing solution 145 is then passed to cation exchange column 146. An eluent is introduced to column 146, which causes elution 147 of the $Hg^{2+}$ and R—$Hg^+$ species at different rates. This separated (speciated) solution 148 is then passed to oxidation 150 where the R—$Hg^+$ species is oxidized to $Hg^{2+}$. If inductively coupled plasma spectroscopy (ICP) is the selected form of analysis, solution 148 may be passed directly to analysis without oxidation 150. If ICP or atomic adsorption (AA) spectroscopy is the selected form of analysis, solution 148 may be passed directly to reduction 170, for combination with a hydride reductant.

Solution 155, now containing mercury as $Hg^{2+}$, is passed to optional prereduction 160. Optional prereduction 160 can deactivate remaining active oxidizing species, and partially reduce the mercury. Partially-reduced solution 165 is then passed to reduction 170 where $Hg^{2+}$ species are converted to the elemental form of mercury ($Hg^{\circ}$). Solution 175, containing elemental mercury, is then passed to volatilization 180. Volatilized mercury contained in a gas stream 185 is then passed to analysis 190. During analysis 190, the separate $Hg^{\circ}$ peaks are quantified. Because the $Hg^{2+}$ and R—$Hg^+$ species were previously separated, the quantity of each may be determined from the areas of their corresponding $Hg^{\circ}$ peaks.

Possible quantitation methods performed during analysis 190 include ICP, ICP-mass spectroscopy (MS), AA, cold vapor atomic absorption spectroscopy (CVAAS), and fluorescence. Most preferably, analysis 190 includes cold vapor atomic fluorescence spectroscopy (CVAFS).

Collection (110)

The water sample for analysis may be collected from any aqueous source that contains mercury, including, but not limited to, streams, lakes, rivers, ponds, drinking water supplies, irrigation systems, and wells. Samples may also be collected that require digestion, such as when biological tissue is digested with strong acid or base, or extraction, such as when sediment is extracted with thiourea. Optionally, the sample may be filtered to remove any particulate matter before further processing.

Many methods are known to collect a sample for mercury analysis. The Environmental Protection Agency has released very detailed protocols to prevent pre- or post-contamination of the sample. While any suitable method may be used with the preferred embodiments, a preferred method is based on the "clean-hands," "dirty hands" protocol.

Briefly, in this protocol, sample containers (generally Teflon or borosilicate glass) are rigorously cleaned first in hot (60-70° C.) concentrated nitric acid overnight or hot (60-70° C.) 4N HCl for 48 hours, followed by filling with a 1% (weight/volume) HCl solution and heating in a 60° C. oven overnight. This solution is then replaced with a 0.5% (weight/volume) ultrapure HCl solution and left in the bottle until sampling. The acid is dumped immediately before filling the bottle from the water source. The bottles are capped tightly after removal from the oven and double bagged in polyethylene "zip-type" bags. Bagged bottles are placed in an acid-rinsed clean cooler for transport to the sampling site.

At the sampling site, two people are required for clean sampling. Personnel doing the sampling generally wear clean, powder-free, class 100 compliant gloves, and, preferably, TYVEC suits. The first person (dirty-hands) opens the first bag to expose the second bag, which is taken out and opened by the second person (clean hands). The second person dumps the 0.5% (weight/volume) HCl solution away from the water source to be sampled, dips the bottle below the surface of the water, and caps the bottle while excluding all air. The sampler then places the bottle back into the clean inner bag and seals it. The inner bag is then transferred to the outer bag held by the first person, who then seals the outer bag. The samples are then put on ice in the cooler and transported back to the clean lab for processing and analysis.

Acidification (120)

To dissociate the mercury analytes, whether $Hg^{2+}$ or $R—Hg^+$, from the organic and sulfide matrix interferents where they naturally reside, acidification is utilized. Once acidified, the solution is allowed to react for preferably, from about 30 minutes to about one week, more preferably from about 1 hour to about 1 day, and most preferably overnight (i.e., about 12 hours), before subsequent processing. This time period varies on the source water and degree of acidification.

While not wishing to be bound by any particular theory, it is believed that matrix interferents, which are present in natural water, complex with the mercury species and bind them in the sample matrix. Dissolved organic matter (DOM) and sulfide or bisulfide ions ($S^{-2}$ and $HS^-$) are two examples of matrix interferents. These interferents are believed to "mask" the mercury species, thus inhibiting adsorption of the mercury onto chelating resins.

Matrix interferents are believed to adhere most effectively to mercury species at moderate pH ranges, between pH=4-9, for example, and their binding strength is believed to diminish with decreasing pH. As these natural ligands become protonated due to decreasing pH, it is believed that they lose their ability to bind the mercury, thus, releasing it from the sample matrix.

For example, at low pH the masking ligand $HS^-$ is protonated to form $H_2S$, a gas that can leave the solution. Once the $HS^-$ ligand is protonated, it can no longer bind the mercury species, thus releasing the mercury from the sample matrix. Because the acidification can release $Hg^{2+}$ and $R—Hg^+$ species from the sample matrix, a single post-acidification analysis method can be used to separate and quantify both species.

During acidification 120, a strong acid is added to the collection sample 115. While any strong acid may be used to lower pH, hydrogen-halide acids, such as HCl or HBr, are preferred due to their ability to fully ionize in water, their low oxidizing power, and their ability to bind mercury. A solution containing from 1 to 3% (weight/volume) HCl in water is most preferred.

Acid is preferably added to collection sample 115, or a portion of the sample, until a low sample pH is achieved. As used in the following specification and appended claims, "low sample pH" is defined as $pH \leq 2.5$, more preferably $pH \leq 2$, most preferably $pH \leq 1.5$, and even more preferably $pH \leq 1$. Once low sample pH is achieved, acidified sample 125 is preferably passed to preconcentration 130.

Preconcentration (130)/Desorption (140)

Preconcentration can be utilized to increase the quantity of mercury available for analysis. This is often necessary because mercury is commonly found at sub-nanogram per Liter concentrations, particularly in water supplies. During preconcentration 130, the $Hg^{2+}$ and $R—Hg^+$ species are removed from the acidified water sample and concentrated, through adsorption onto a resin. Although not required, the preconcentration resin is often packed into a column. While acidification 120 releases the mercury species (especially monomethylmercury) from the sample matrix, the pH of the resultant solution is too low for conventional preconcentration columns to efficiently adsorb the mercury.

A preferred preconcentration resin is modified with adsorption ligands that maintain adsorption capacity at low sample pH. In addition to being able to adsorb the mercury species at low pH levels, the preferred preconcentration resin does not bind the mercury so strongly that it cannot be eluted from the resin for further analysis.

In a preferred embodiment, a thiourea ($H_2NC(S)NH_2$) modified preconcentration resin is utilized. Thiourea is preferred as an adsorption ligand because it is able to quantitatively remove (adsorb) the $Hg^{2+}$ and $R—Hg^+$ species from the low pH solution onto the modified preconcentration resin. By quantitatively, it is meant that preferably more than 50%, more preferably, more than 80%, and most preferably, more than 98% of the $Hg^{+2}$ and $Hg^{+1}$ species in solution are adsorbed from the low pH solution.

In addition to quantitative removal of the $Hg^{2+}$ and $R—Hg^+$ species from the low pH solution, the preferred preconcentration resin allows for consistent desorption of the $Hg^{2+}$ and $R—Hg^+$ species from the resin. Consistent desorption is defined as being able to perform ten consecutive adsorption/desorption cycles wherein preferably at most 5% (M/M) of the total mercury is retained on the preconcentration resin after the tenth desorption, more preferably at most 2% (M/M), and most preferably at most 0.5% (M/M). For example, if a solution has a 1 M combined concentration of $Hg^{2+}$ and $R—Hg^+$ species and is adsorbed and desorbed from the preconcentration column ten consecutive times, at least a 0.95 M solution of $Hg^{2+}$ and $R—Hg^+$ species is recovered from the tenth desorption.

While sulfide, dithiocarbamate, or other adsorption ligands that would more strongly bond the $Hg^{2+}$ and $R—Hg^+$ species could be used, the performance of these resins decreases at the low sample pH of acidified solution 125. The preferred thiourea-modified preconcentration resin is believed to resist protonation even at $pH \leq 1$.

After the $Hg^{2+}$ and $R—Hg^+$ species are adsorbed onto the preconcentration resin in preconcentration 130, desorption 140 is performed. During desorption 140, a solution containing bifunctional moieties is pumped through the preconcentration resin, which desorbs or liberates the $Hg^{2+}$ and $R—Hg^+$ species from the resin. Preferably, this desorption solution is an acidified thiourea solution containing competing cations. In one embodiment, the desorption solution is the same eluent used in elution 147, as described below.

While not wishing to be bound by any particular theory, the desorption solution is believed to more strongly bond the $Hg^{2+}$ and $R—Hg^+$ species than the resin modified with thiourea. Because the preferred desorption solution contains thiourea, it is believed to provide the added benefit of replacing any thiourea lost from the modified resin, thus, extending the useful life of the preconcentration resin.

Bifunctional moieties are defined as neutral compounds that can adsorb the mercury from the sample at low sample pH when used as a resin modifier, and then desorb the mercury from the modified resin when used in a desorption solution. Thiourea is the most preferred bifunctional moiety because it can serve as both the resin modifier and in the desorption solution to desorb the mercury from the resin. Thiocarbamates may also be used as a resin modifiers.

While not wishing to be bound by any particular theory, it is believed that when used as a resin modifier, the sulfur atom of thiourea is bound to the resin, thus making only the amino ($NH_2$) groups of thiourea available for binding the $Hg^{2+}$ and R—$Hg^+$ species. Alternatively, when used as an eluent, the sulfur atom of thiourea is believed to be available for bonding with the $Hg^{2+}$ and R—$Hg^+$ species, thus forming a stronger bond with the mercury than the amino groups. Therefore, when associated with the thiourea-modified resin, mercury is thought to be datively bound as depicted below

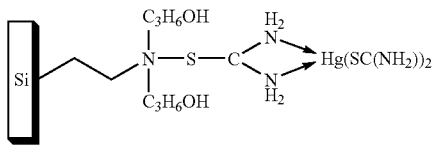

and when eluted by thiourea, mercury is thought to be bound as

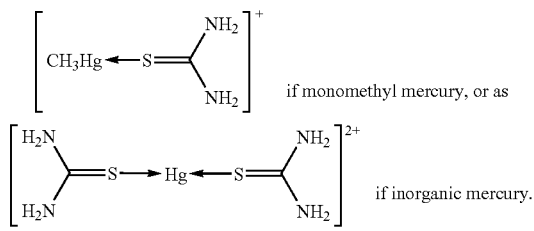

It is important to note, that because thiourea is neutral, when associated with the $Hg^{2+}$ and R—$Hg^+$ species, a cationic complex results. While thiourea is the most preferred bifunctional moiety, any compound that provides the ability to uptake the $Hg^{2+}$ and R—$Hg^+$ species at low sample pH when used as a resin modifier, and desorb the mercury species when used as an eluent component is a preferred bifunctional moiety.

The preferred, thiourea-modified preconcentration resin can be made by refluxing 3-aminopropyl silica gel (APSG) with thiourea. A more complete description of how to prepare a thiourea-modified resin is found in Liu et al., *Synthesis of silica gel immobilized thiourea and its application to the on-line preconcentration and separation of silver, gold and palladium*, Analyst, (2000), 125, 147-150, the contents of which are incorporated herein by reference. The thiourea-modified resin may then be packed into a column by any conventional method. In a preferred embodiment, the modified resin is sent to Column Engineering, Inc., Ontario, Calif., for packing.

While the average effective particle diameter of the resin used during preconcentration can vary broadly, preferably the average effective diameter of the particles is from 3 to 200 micrometers (μm), more preferably from 20 to 100 μm, and most preferably from 30 to 70 μm. While smaller particle diameters may allow more efficient adsorption of mercury from solution, as their average effective diameter decreases, it becomes more difficult to pump the solution through a column packed with the resin particles. By "average effective particle diameter" it is meant the average of the longest dimension of the particles. Thus, if a particle is 10 μm in one dimension and 100 μm in another, the effective diameter of that particle is 100 μm. An average is determined from the effective particle diameter of multiple particles.

Thiourea may be added to the mercury-containing sample during acidification 120, thus pre-complexing thiourea with the $Hg^{2+}$ and R—$Hg^+$ species. In this instance, preconcentration 130 could rely on a cation exchange resin for preconcentration of the $Hg^{2+}$ and R—$Hg^+$ species, and not require a thiourea-modified resin.

Autosampler

Figure 4:
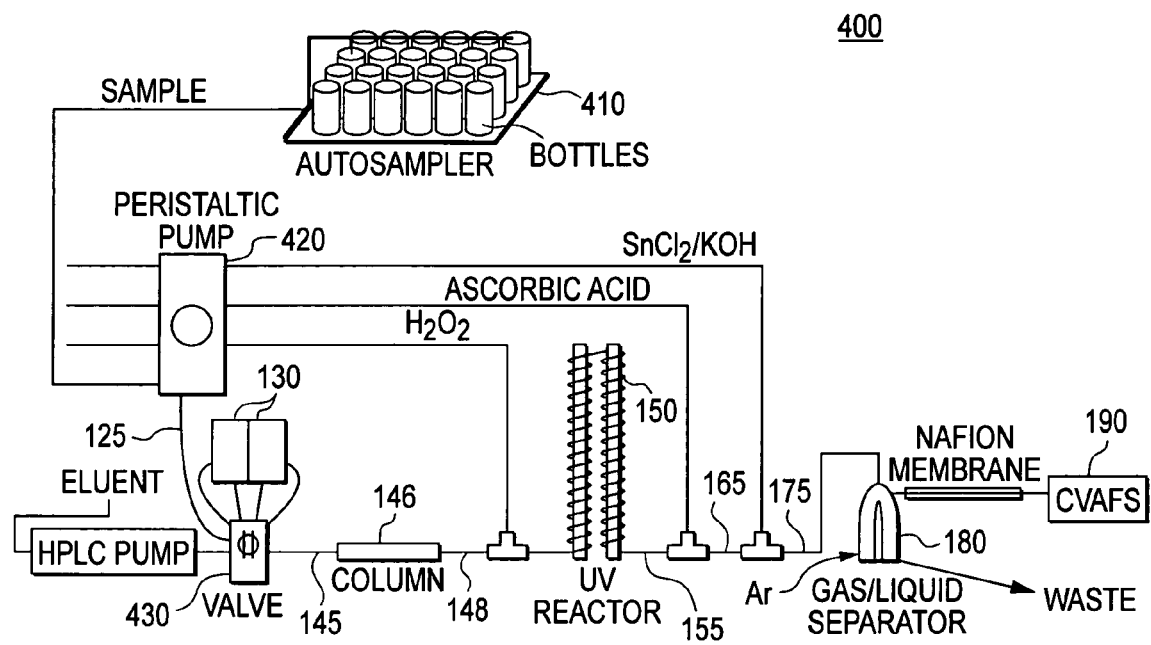
FIG. 4 is a depiction of an exemplary apparatus for mercury analysis.

Referring to FIG. 4, in one exemplary embodiment device 400 includes an autosampler 410 that can be used to preconcentrate multiple acidified samples. For example, an autosampler consisting of a computer-controlled robotic sampling mechanism can withdraw samples from 250 mL Teflon bottles. The autosampler also has an uptake run by a peristaltic or similar pump 420 that is capable of producing pressures adequate to pass the solution through preconcentration 130. Additionally, the autosampler has a reservoir for an acidic solution (4 N HCl, for example) for cleaning the sampling needle and flushing the delivery tubing between samples.

Sample uptake preferably occurs for a period of time sufficient for appropriate preconcentration volumes to be obtained. For example, samples containing lower concentrations of mercury will require longer preconcentration periods than higher concentration samples. The samples may be pre-weighed to determine the initial volume and weighed again after analysis to determine the exact amount of sample preconcentrated.

Preferably, the autosampler uses a high-pressure, 10-position switching valve 430 that holds two preconcentration columns in separate loops. In this manner, one column can preconcentrate a sample, while the other is eluting the previous sample as 145 into cation exchange column 146. Computer software can control the sequence and timing of events during sample preconcentration and desorption.

Cation Exchange Column (146)

In a preferred embodiment, mercury containing solution 145, which contains a mixture of $Hg^{2+}$ and R—$Hg^+$ species believed to be bound to thiourea, is passed to cation exchange column 146. Cation exchange column 146 contains one or more cation exchange resins having anionic sites that can associate the cationic $Hg^{2+}$ and R—$Hg^+$ species. Preferably, a cation exchange column may also include cation exchange resins having cationic sites. As defined herein, a cation exchange resin can be any resin or group of resins, which in combination can associate and dissociate cations, regardless of the polarity on the surface of an individual resin. Thus a cation exchange resin can contain individual resin particles that only associate cations and individual resin particles that only associate anions, as long as in combination, the resins associate cations.

Cationic $Hg^{2+}$ and R—$Hg^+$ species are believed to repeatedly associate and dissociate with the anionic sites contained within the column. By varying the amount of anionic versus cationic resin in the cation exchange column, its performance can be tuned. When a preferable eluent is introduced onto the column, elution 147 occurs as the cationic $Hg^{2+}$ and R—$Hg^+$ species are dissociated.

Any cation exchange column that provides the desired separation or speciation of the $Hg^{2+}$ and R—$Hg^+$ species during elution 147 may be used. Preferably, a Dionex IONPAC CG5A mixed mode exchange column, available from Dionex, Inc., 501 Mercury Dr., Sunnyvale, Calif. is utilized.

Elution (147)

During elution 147, the eluent removes the associated $Hg^{2+}$ and R—$Hg^+$ species from the cation exchange column. Preferably, the eluent is aqueous and contains a bifunctional moiety, protons, and competing cations. Thiourea is the most preferred bifunctional moiety.

While not wishing to be limited by any particular theory, it is believed that thiourea bound $Hg^{2+}$ and R—$Hg^+$ species associate with the anionic sites of the cationic exchange column. Then, as the eluent is introduced, thiourea maintains the integrity of the mercury-thiourea complexes, while the protons and competing cations compete for the anionic sites on the column. In this fashion, the mercury-thiourea complexes are believed to be dissociated.

Although an eluent containing a combination of a bifunctional moiety and an acid without the competing cations can at least partially dissociate the R—$Hg^+$ species, to dissociate the more strongly associated $Hg^{+2}$ species, multivalent competing cations are preferred. Depending on the concentration of protons and competing cations in the eluent and the rate at which the eluent is introduced onto the column, the separation and elution rate of the $Hg^{2+}$ and R—$Hg^+$ species can be controlled.

Figure 2:
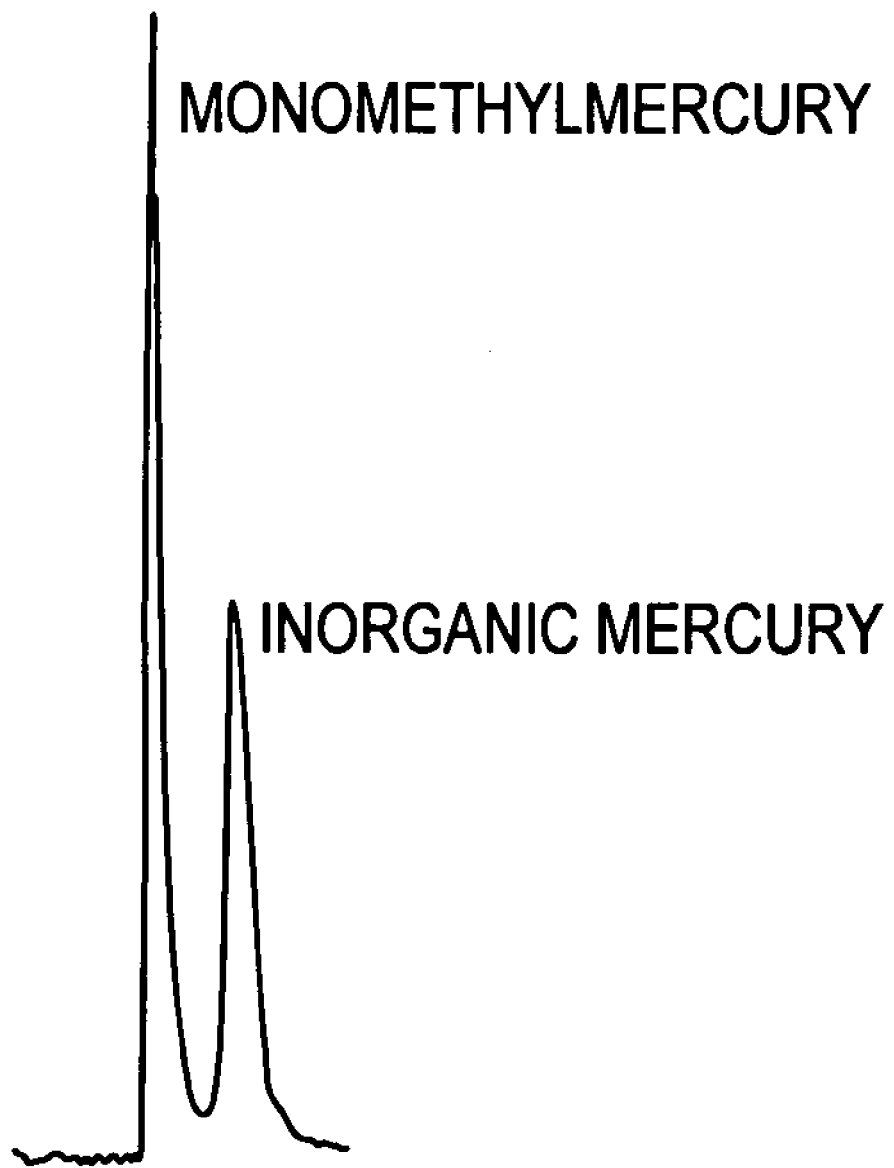
FIG. 2 depicts sample separation peaks for inorganic and monomethyl mercury.

To independently quantify the thiourea complexed $Hg^{2+}$ and R—$Hg^+$ species with a single method, the eluent is preferably able to selectively dissociate one, then the other, mercury species from the column. Referring to FIG. 2, the $Hg^{2+}$ (inorganic) mercury can be cleanly separated from monomethylmercury. While in a preferred embodiment the R—$Hg^+$ species elutes first, this is not required. After elution 147, the eluent 148, which now contains the separated mercury complexes, is subsequently processed in a manner that maintains the separation between the $Hg^{2+}$ and R—$Hg^+$ portions of the sample.

The eluent introduced during elution 147, preferably contains a bifunctional moiety, protons, and competing cations in an aqueous solution. Thiourea is the most preferred bifunctional moiety. The eluent is preferably from 0.1% to 10% thiourea (weight/volume), more preferably from 0.5% to 5% thiourea (weight/volume), and most preferably from 1% to 2% thiourea (weight/volume). While any strong acid may be used as a source of protons that results in the desired separation and is compatible with the bifunctional moiety complexed $Hg^{2+}$ and R—$Hg^+$ species and the cationic exchange column, hydrogen-halide acids are preferred. Hydrochloric acid is most preferred. The eluent is preferably at least 0.1% (weight/volume) acid, more preferably at least 3% (weight/volume) acid, and most preferably at least 5% (weight/volume) acid. The eluent preferably has a competing cation concentration of from 1 millimolar (mM) to 15 mM, more preferably from 3 mM to 10 mM, and most preferably from 4 mM to 7 mM. For example, the eluent could be 1.5% thiourea (weight/volume), 7% HCL (weight/volume), 5 mM $Mg^{2+}$, and 5 mM $Ca^{2+}$.

While any salt that generates a sufficient number of competing cations in the eluent to dissociate the mercury species from the cation exchange column may be utilized, salts that generate $Li^+$, $Na^+$, $K^+$, $Ti^{+2}$, $V^{+2}$, $Cr^{+3}$, $Co^{+2}$, $Ni^{+2}$, $Fe^{+2}$, $Mn^{+2}$, $Rh^{+2}$, $Ru^{+2}$, $Cd^{+2}$, $Sn^{+4}$, $Pb^{+2}$, $Ag^{30}$, $Mn^{+4}$, $Fe^{+3}$, $Cu^{+1}$, $Cu^{+2}$, $Zn^{+2}$, $La^{+3}$, $Ba^{+2}$, $Sr^{+2}$, $Ca^{+2}$, $Mg^{+2}$, $Al^{+3}$ or $Au^{+3}$ cations are preferred. Salts that generate $Ca^{+2}$, $Mg^{+2}$, $Al^{+3}$, $Mn^{+4}$, $Fe^{+3}$, $Cu^{+1}$, $Cu^{+2}$, $Zn^{+2}$, $La^{+3}$, $Ba^{+2}$, and $Sr^{+2}$ cations are more preferred. Salts that generate $Ca^{+2}$, $Mg^{+2}$, and $Al^{+3}$ cations, such as calcium chloride, magnesium chloride, or aluminum chloride, are most preferred.

While a single competing cation could be used, an approximately 1:1 mixture of two multivalent cations, such as calcium and magnesium, is most preferred. Multivalent is defined as having a formal oxidation state of $^+2$ or greater. Mixing two or more cations can provide precipitation resistance to the solution during reduction 170.

While not wishing to be bound by any particular theory, it is thought that if a sufficient quantity of a single competing cation is used, it can reach a concentration where it is likely to precipitate in strong hydroxide solutions. However, by using a mixture of two or more competing cations, a high competing cation concentration can be achieved in the eluent, without any single cation being present in sufficient concentration to precipitate during reduction 170. For example, if X competing cation concentration is preferred to effectively disassociate the mercury species from the cation exchange column, and X concentration of a single cation will precipitate during reduction 170, by utilizing a X/2 cation concentration of a calcium salt, and a X/2 concentration of a magnesium salt, the mercury species can be effectively eluted, and precipitation avoided.

Gradient Method

If gradient elution from cation exchange column 146 is used in concert with thiourea addition during acidification 120, preconcentration and separation (130 through 148) can occur on a single column. By adding a bifunctional moiety during acidification 120 and by using two or more eluents in a gradient, the same cation exchange column that concentrates the $Hg^{2+}$ and R—$Hg^+$ species can be used to separate them. In a gradient elution, two or more eluent combinations are used to elute the column.

For example, if thiourea-mercury complexes are formed during acidification 120, the thiourea complexed $Hg^{2+}$ and R—$Hg^+$ species may be concentrated on a cation exchange column. The cation exchange column may then be first eluted with a first eluent containing thiourea and HCl, to disassociate the R—$Hg^+$ species. A second eluent containing thiourea, HCl, and competing cations, such as $Mg^{2+}$ and $Ca^{2+}$, may then be introduced onto the column to elute the more strongly bound $Hg^{2+}$ species. In this manner, preconcentration and separation are conducted on a single column.

The rate and percentage of first versus second eluent introduced onto the cation exchange column is referred to as the gradient. Preferably, this gradient is obtained through computer control of an automated eluent mixing and pumping apparatus.

Oxidation (150)

Eluent solution 148, containing the $Hg^{2+}$ and R—$Hg^+$ species, in addition to thiourea, protons, and competing cations, is passed to oxidation 150. Oxidation 150 converts the R—$Hg^+$ species into $Hg^{2+}$ species. While any oxidation method that quantitatively converts the R—$Hg^+$ species into a $Hg^{2+}$ species and is compatible with eluent solution 148 is preferred, most preferred is an oxidation method where hydrogen peroxide is introduced during oxidation 150 and the resultant solution is then exposed to ultraviolet light 156 to form oxidized solution 155. In this instance, quantitatively means that preferably more than 50%, more preferably, more than 80%, and most preferably, more than 98% of the $Hg^{+1}$ species in solution are oxidized to $Hg^{+2}$ species.

Preferably, a 2% to 20% (weight/volume) hydrogen peroxide solution is introduced during oxidation 150 prior to irradiation with ultraviolet light. Most preferably, a 5% (weight/volume) solution is introduced. While any appropriate source of ultraviolet light may be used, preferably, the solution is passed through a TEFLON tube surrounding a pair of 8 watt low-pressure UV bulbs (254 nm radiation).

Prereduction (160)

Oxidized solution 155 is optionally passed to prereduction 160 to form prereduction solution 165. During oxidation 150, excess active oxidizing species, such as free radicals, may be generated. During optional prereduction 160, an anti-oxidant is added to deactivate any excess active oxidizing species that may be present. Additionally, during prereduction 160, the competing cations are complexed to further impede their interference, generally in the form of precipitation, with reduction 170. Preferably, the prereduction agent slightly reduces the $Hg^{2+}$ species present in solution.

While independent compositions can be used to perform the independent functions of deactivating excess oxidizing species and complexing the competing cations, a single agent is preferred. If independent compositions are used, citric acid may be used to complex the competing cations, while hydroxylamine may be used to deactivate the excess oxidizing species. In a preferred embodiment, ascorbic acid is used because it can serve both as an anti-oxidant and as a complexing agent for the competing cations. Preferably an aqueous solution is introduced that contains from 2% to 40% (weight/volume) ascorbic acid, more preferably from 5% to 30% (weight/volume) ascorbic acid, and most preferably from 10% to 20% (weight/volume) ascorbic acid.

Reduction (170)

Prereduction solution 165 is passed to reduction 170. During reduction 170, the $Hg^{2+}$ species are quantitatively reduced to elemental mercury ($Hg^{\circ}$). In this instance quantitatively means that preferably more than 50%, more preferably, more than 80%, and most preferably, more than 98% of the $Hg^{+2}$ species in solution are reduced to $Hg^{\circ}$. Preferably, any reducing agent that can convert $Hg^{2+}$ species to elemental mercury may be used, including hydride sources, such as sodium borohydride or potassium borohydride, for example. When analysis 190 relies on fluorescence, however, a basic solution of stannous chloride (Sigma Chemicals, St. Louis, Mo.) is preferred.

If analysis 190 relies on fluorescence detection, an aqueous solution of from 2% to 10% (weight/volume) stannous chloride in 40% (weight/volume) potassium hydroxide is most preferably used for reduction. If analysis 190 does not rely on fluorescence detection, such as for atomic adsorption or inductively coupled plasma (ICP) spectroscopy, hydride source reductants are most preferred.

Volatilization (180)

Solution 175, which contains mercury in its elemental state, is then passed to volatilization 180. During volatilization 180, an inert gas, such as argon, is passed through or across solution 175 to uptake the elemental mercury as a vapor. This inert gas stream, now containing mercury, is then dried. While any method which removes water vapor is preferred, more preferable drying techniques include passing the gas stream through a column containing a desiccant, such as magnesium perchlorate, or through a membrane-type drying tube, such as a NAFION drying tube (PERMAPURE, Toms River, N.J.).

Analysis (190)

Figure 3:
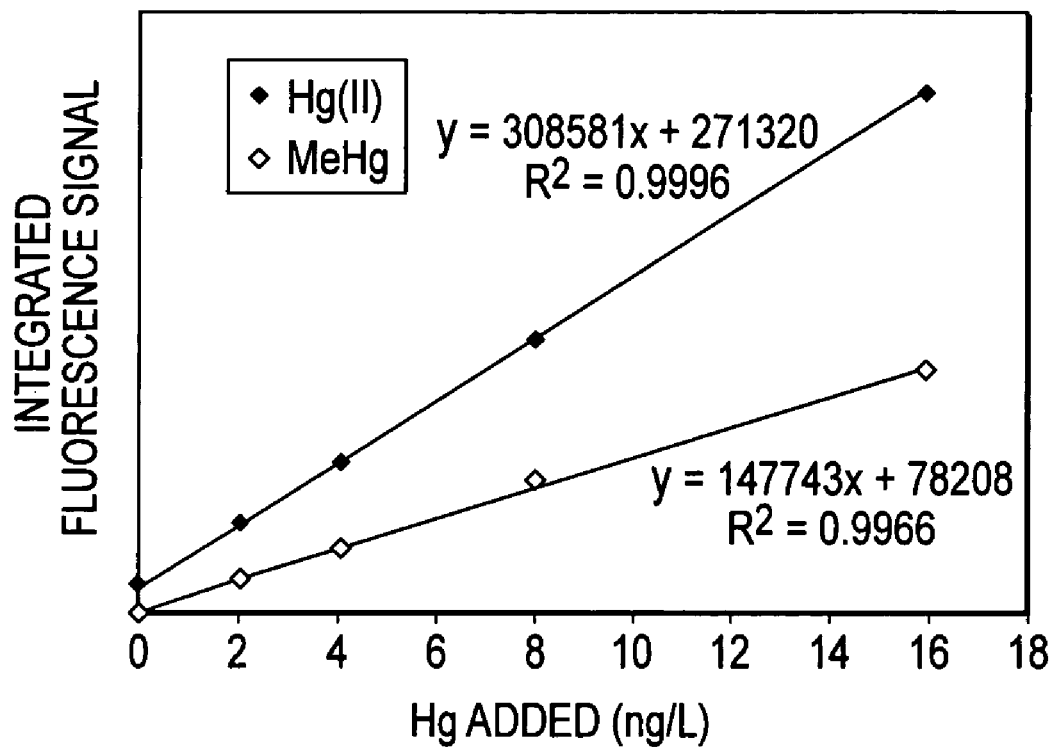
FIG. 3 depicts a sample calibration curve for inorganic and monomethylmercury.

Gas stream 185 is then passed to analysis 190. Analysis can involve any analytical method capable of detecting, and preferably determining the quantity of, or quantifying, mercury. Due to heightened sensitivity, atomic fluorescence detection methods, such as cold vapor atomic fluorescence spectroscopy (CVAFS), are most preferred. However, atomic absorption (AA), ICP, and mass spectroscopy methods are also anticipated. FIG. 3 shows a calibration curve that may be used to determine the quantity of $Hg^{2+}$ and $R-Hg^+$ species present in a collected sample from an atomic fluorescence signal. Preferably, $Hg^{2+}$ and $R-Hg^+$ species can be detected and quantified in samples down to 0.1 ppt, more preferably down to 0.01 ppt, and most preferably down to 0.001 ppt. While these ranges are preferred, because large sample volumes (>200 mL) can be preconcentrated, detection and quantification below 0.001 ppt is possible if sufficient sample is preconcentrated.

While gas stream 185 contains the collected mercury, whether arising from $Hg^{2+}$ or $R-Hg^+$ species, as elemental mercury ($Hg^{\circ}$), it is the separation that occurred during elution of the cation exchange column, which is preserved during further processing, that allows for quantitation of inorganic verses organic mercury. Referring again to FIG. 2, two separate peaks are detected.

The preceding description is not intended to limit the scope of the invention to the preferred embodiments described, but rather to enable any person skilled in the art of analytical chemistry to make and use the invention.

EXAMPLES

Example 1

Analysis of a Mercury Containing Water Sample when Thiourea is not Added During Acidification.

a) Collected Sample Preparation

A water sample containing mercury and natural organic matter (Suwannee River Natural Organic Matter, available from the International Humic Substances Society, University of Minnesota, St. Paul, Minn.) was acidified to pH=1.0 with Optima Grade super-pure 37% concentrated HCl. The acidified solution was allowed to equilibrate overnight.

b) Calibration Solution Preparation

While the samples equilibrated, five aqueous calibration solutions were prepared with known mercury concentrations bracketing the range of expected mercury concentrations in the water sample. An appropriate volume (e.g. 50 mL or less for solutions containing greater than 0.5 ppt (parts per trillion or nanograms per Liter) monomethylmercury, 50-100 mL for solutions containing 0.1-0.5 ppt monomethylmercury, 100-200 mL for solutions containing 0.01-0.1 ppt monomethylmercury, and >200 mL for solutions containing less than 0.01 ppt monomethylmercury) of the each calibration solution was then pumped into a separate TUSG preconcentration column.

c) System Calibration

While the high-pressure switching valve of the separation system was in the load position, a preconcentration column loaded from one of the calibration solutions was placed in the column holder within the sample loop of the high-pressure switching valve. The valve was then switched to the inject position to desorb the adsorbed $Hg^{2+}$ and $R-Hg^+$ species into the analytical system. The eluent was an aqueous solution containing 1.5% thiourea (weight/volume), 7% HCL (weight/volume), 5 mM $MgCl_2$, and 5 mM $CaCl_2$.

The $Hg^{2+}$ and $R-Hg^+$ species were then separated across a 4.0×50 mm cation exchange column (Dionex IONPAK CG5A) and sequentially oxidized with hydrogen peroxide and ultraviolet light, reduced with ascorbic acid and stannous chloride to $Hg^\circ$, and removed as a gas stream from the eluent discharge stream. The elemental mercury containing gas stream was then routed to a fluorescence detector, where the individual peaks arising from the initial $Hg^{2+}$ and $R-Hg^+$ species peaks were detected. This was repeated for each preconcentration column loaded with calibration solution. Fluorescence linearly correlated with mercury concentration, as may be seen in FIG. 3. A data integrator was used to record and integrate the area of the peaks over the instrument baseline so quantitative analysis could be performed.

d) Calibration Curve Preparation

The volume of calibration solution passed across the preconcentration column was multiplied by the concentration of the standard solution to obtain the absolute weight of $Hg^{2+}$ and $R-Hg^+$ species preconcentrated at each concentration level. Using EXCEL, or similar graphing software, an equation was obtained for a line relating fluorescence peak area to absolute $Hg^{2+}$ and $R-Hg^+$ species weight preconcentrated. Correlation $R^2$ was better than 0.999. The equation for the line was then used to calculate the absolute weight of preconcentrated samples, which was then converted to concentration by dividing by the sample volume preconcentrated. Determining separate calibration curves for the $Hg^{2+}$ and $R-Hg^+$ species was found to be slightly more accurate due to the differing background contamination levels.

e) Sample Analysis

After equilibration of the sample with the added HCl, a peristaltic pump was used to pump a volume of the sample appropriate to the range of concentrations of the calibration samples across a preconcentration column (see Calibration Solution Preparation above). The sample was then desorbed from the preconcentration column and analyzed for $Hg^{2+}$ and $R-Hg^+$ species as described for the calibration solutions under System Calibration.

Example 2

Synthesis of the Thiourea-Modified Preconcentration Resin

The Thiourea-modified silica gel (TUSG) used as a preconcentration resin was synthesized as follows. Five grams of 3-aminopropyl silica gel (APSG) (40-63 μm particle size) was obtained from Sigma-Aldrich (Milwaukee, Wis.). This silica gel was combined with 5 grams of thiourea (Sigma-Aldrich, Milwaukee, Wis.), which was previously ground with a mortar and pestle, in 30 mL of xylene. The xylene was distilled from $CaSO_4$. The mixture was refluxed gently in a 125 mL round-bottom flask for about six hours while being gently stirred by a magnetic stirrer.

The Thiourea-modified resin was a yellow-orange color and was collected onto a 0.7 μm glass fiber filter, washed with ethanol, washed with deionized water, and then dried under an infra-red bulb. Once dry, the modified resin was stored until being sent to Column Engineering, Inc., Ontario, Calif., for packing into microcolumns.

Prophetic Example 1

Analysis of a Mercury Containing Water Sample when Thiourea is Added During Acidification a) Collected Sample Preparation Rigorously acid-cleaned Teflon™ bottles are used to collect environmental samples of mercury containing water. These samples are acidified with Optima Grade or other super-pure 37% concentrated HCl to a pH of 2.0 or less. A three molar thiourea solution is then added to bring each sample to a thiourea concentration of 50 mM. The samples are allowed to equilibrate overnight.

b) Calibration Solution Preparation

Five calibration solutions are prepared with known mercury concentrations that bracket those expected in the collected samples, as in Example 1b, except that HCl and thiourea are added as for the collected samples from step (a) of this example. An appropriate volume of each calibration solution, determined as in Example 1, is then pumped across a preconcentration column containing one or more resins, at least one of which has cation exchange functionality.

c) System Calibration

While the high-pressure switching valve of the separation system is in the load position, a loaded preconcentration column is placed in the column holder within the sample loop of the high-pressure switching valve. The valve is then switched to the inject position to desorb the adsorbed $Hg^{2+}$ and $R-Hg^+$ species into the analytical system.

The $Hg^{2+}$ and $R-Hg^+$ species are then separated across a 4.0×50 mm cation exchange column (Dionex IONPAK CG5A) with an eluent containing 0.1% (weight/volume) thiourea, 7% (weight/volume) HCl, 5 mM $CaCl_2$, and 5 mM $MgCl_2$. As in Example 1, the separated species are then sequentially oxidized, reduced, and removed as a gas from the eluent stream. The gas is then sent to a fluorescence detector, where the individual peaks are detected and integrated so a calibration curve can be determined, as in Example 1.

d) Sample Analysis

After equilibration of the sample with the added HCl and thiourea, a peristaltic pump is used to introduce an appropriate sample volume onto the cationic preconcentration column. The sample is then desorbed from the preconcentration column and analyzed for $Hg^{2+}$ and $R-Hg^+$ species as described for the calibration solutions.

Prophetic Example 2

Analysis of a Mercury Containing Water Sample Using a Single Column with Gradient Elution.

As outlined in Prophetic Example 1, collected samples and calibration solutions are prepared that include acid and thiourea. In this method, however, the samples and solutions are not adsorbed first onto a preconcentration column and then separated on another (the analytic) column. Instead, a single cation exchange column is used, but with gradient elution, as outlined below.

An appropriate amount of the collected sample or a calibration solution is introduced onto the column, depending on mercury concentration, as outlined above. While the high-pressure switching valve of the system is in the load position, the loaded column is placed in the column holder within the sample loop of the high-pressure switching valve. The valve is then switched to the inject position to elute the trapped $Hg^{2+}$ and $R-Hg^+$ species with a gradient of at least two eluent solutions. Eluent A has a concentration of 0.1% (weight/volume) thiourea and 7% (weight/volume) HCl. Eluent B has a concentration of 0.1% (weight/volume) thiourea, 7% (weight/volume) HCl, 5 mM $CaCl_2$, and 5 mM $MgCl_2$. The gradient program first flushes the column with 100% eluent A to fully elute the $R-Hg^+$ species. After an appropriate time, the gradient then begins introducing eluent B, until 100% eluent B is reached, to elute the $Hg^{2+}$ species. The gradient resets to eluent A between samples.

As any person skilled in the art of analytical chemistry will recognize from the previous description, figures, and examples that modifications and changes can be made to the preferred embodiments of the invention without departing from the scope of the invention defined by the following claims.

What is claimed:

1. A method for mercury analysis of a sample, comprising:
   fractionating the sample comprising inorganic mercury and organic mercury species on a cation exchange resin, to produce a first fraction comprising organic mercury species and a second fraction comprising inorganic mercury species;
   oxidizing the first fraction to inorganic mercury;
   reducing the first fraction to elemental mercury;
   reducing the second fraction to elemental mercury;
   volatilizing the first fraction;
   volatilizing the second fraction;
   quantifying mercury content present in the first fraction; and
   quantifying mercury content present in the second fraction;
   wherein the first fraction is separated from the second fraction;
   wherein fractionating comprises:
      absorbing the sample on the cation exchange resin under conditions that promote retention of inorganic mercury and organic mercury species on the cation exchange resin;
      washing the cation exchange resin to remove at least one non-mercury contaminant of the sample from the cation exchange resin without simultaneously removing mercury content of the sample from the cation exchange resin; and
      eluting inorganic mercury and organic mercury species in separate fractions from the cation exchange resin;
      wherein the eluting is carried out with an aqueous eluent comprising a bifunctional moiety and a source of protons.

2. The method of claim 1, wherein the cation exchange resin is a mixed mode ion exchange resin.

3. The method of claim 1, wherein
   the first fraction comprises at least 98 percent of all organic mercury species in the sample with at most 2 percent contaminating inorganic mercury species, and
   the second fraction comprises at least 98 percent of all inorganic mercury species in the sample with at most 2 percent contaminating organic mercury species.

4. The method of claim 1, wherein the first and second fractions are substantially free of matrix interferents.

5. The method of claim 1, wherein the aqueous eluent comprises
   the bifunctional moiety comprising thiourea having a final concentration in the aqueous eluent in the range from 0.1% (wt/vol) to 10% (wt/vol); and
   the source of protons is a dissolved acid having a final concentration in the aqueous eluent of at least 0.1% (wt/vol).

6. The method of claim 1, wherein the quantifying of the mercury content present in the first and second fractions comprises performing at least one analytical method selected from the group consisting of atomic absorption, inductively coupled plasma spectroscopy, inductively coupled plasma-mass spectroscopy, and cold vapor atomic fluorescence spectroscopy.

7. The method of claim 1, wherein the quantifying of the mercury content present in the first and second fractions comprises performing cold vapor atomic fluorescence spectroscopy.

8. The method of claim 1, wherein fractionating, oxidizing, reducing, volatilizing, and quantifying occur in an automated system.

9. A method for mercury analysis of a sample, comprising:
   fractionating the sample comprising inorganic mercury and organic mercury species on a cation exchange resin;
   obtaining a first fraction comprising organic mercury species;
   obtaining a second fraction comprising inorganic mercury species;
   quantifying mercury content present in the first fraction; and
   quantifying mercury content present in the second fraction;
   wherein the first fraction is separated from the second fraction; and
   wherein the quantifying of the mercury content present in the first and second fractions comprises independently subjecting the first fraction and the second fraction to one or more different analytical methods.

10. The method of claim 9, wherein the cation exchange resin is a mixed mode ion exchange resin.

11. The method of claim 9, wherein
   the first fraction comprises at least 98 percent of all organic mercury species in the sample with at most 2 percent contaminating inorganic mercury species, and
   the second fraction comprises at least 98 percent of all inorganic mercury species in the sample with at most 2 percent contaminating organic mercury species.

12. The method of claim 9, wherein the first and second fractions are substantially free of matrix interferents.

13. The method of claim 9, wherein fractionating comprises:
   absorbing the sample on the cation exchange resin under conditions that promote retention of inorganic mercury and organic mercury species on the cation exchange resin; and
   eluting inorganic mercury and organic mercury species in separate fractions from the cation exchange resin;
   wherein the eluting is carried out with an aqueous eluent comprising a bifunctional moiety and a source of protons.

14. A method for mercury analysis of a sample, comprising:
   fractionating the sample comprising inorganic mercury and organic mercury species on a cation exchange resin;
   obtaining a first fraction comprising organic mercury species;
   obtaining a second fraction comprising inorganic mercury species;

quantifying mercury content present in the first fraction; and quantifying mercury content present in the second fraction;

wherein the first fraction is separated from the second fraction;

wherein fractionating comprises:

absorbing the sample on the cation exchange resin under conditions that promote retention of inorganic mercury and organic mercury species on the cation exchange resin; and eluting inorganic mercury and organic mercury species in separate fractions from the cation exchange resin;

wherein the eluting is carried out with an aqueous eluent comprising:

a bifunctional moiety comprising thiourea having a final concentration in the aqueous eluent in the range from 0.1% (wt/vol) to 10% (wt/vol); and a source of protons comprising a dissolved acid having a final concentration in the aqueous eluent of at least 0.1% (wt/vol).

15. A method for mercury analysis of a sample, comprising:

fractionating the sample comprising inorganic mercury and organic mercury species on a cation exchange resin;

obtaining a first fraction comprising organic mercury species;

obtaining a second fraction comprising inorganic mercury species;

quantifying mercury content present in the first fraction; and quantifying mercury content present in the second fraction;

wherein the first fraction is separated from the second fraction;

wherein fractionating comprises:

absorbing the sample on the cation exchange resin under conditions that promote retention of inorganic mercury and organic mercury species on the cation exchange resin;

washing the cation exchange resin to remove at least one non-mercury contaminant of the sample from the cation exchange resin without simultaneously removing mercury content of the sample from the cation exchange resin; and eluting inorganic mercury and organic mercury species in separate fractions from the cation exchange resin;

wherein the eluting is carried out with an aqueous eluent comprising a bifunctional moiety and a source of protons.

16. The method of claim 9, wherein the quantifying of the mercury content present in the first and second fractions comprises performing at least one analytical method selected from the group consisting of atomic absorption, inductively coupled plasma spectroscopy, inductively coupled plasma-mass spectroscopy, and cold vapor atomic fluorescence spectroscopy.

17. The method of claim 9, wherein the quantifying of the mercury content present in the first and second fractions comprises performing cold vapor atomic fluorescence spectroscopy.

18. The method of claim 9, wherein fractionating and quantifying occur in an automated system.

19. The method of claim 9, further comprising converting the organic mercury species present in the first fraction and the inorganic mercury species present in the second fraction to elemental mercury.

20. The method of claim 19, wherein converting the organic mercury species present in the first fraction to elemental mercury comprises initially oxidizing the organic mercury species in the presence of hydrogen peroxide and ultraviolet light to form inorganic mercury.

21. The method of claim 20, wherein converting the inorganic mercury present in the first and second fractions to elemental mercury occurs in the presence of a reducing agent selected from the group consisting of sodium borohydride, potassium borohydride, and a basic solution of stannous chloride.

22. The method of claim 19, further comprising volatilizing the elemental mercury prior to quantifying.

23. The method of claim 9, further comprising preconcentrating the sample.

24. A method for mercury analysis of a sample, comprising:

preconcentrating the sample;

fractionating the sample comprising inorganic mercury and organic mercury species on a cation exchange resin;

obtaining a first fraction comprising organic mercury species;

obtaining a second fraction comprising inorganic mercury species;

quantifying mercury content present in the first fraction; and quantifying mercury content present in the second fraction;

wherein the first fraction is separated from the second fraction; and wherein the preconcentrating comprises absorbing the sample onto a resin comprising at least one member selected from the group consisting of a cation exchange resin and a bifunctional moiety comprising a sulfur compound.

25. The method of claim 23, wherein preconcentrating and fractionating the sample occurs on the cation exchange resin.

26. A method for mercury analysis of a sample, comprising:

adsorbing mercury from the sample onto a first resin;

eluting mercury from the first resin, wherein the eluted mercury is substantially free of at least one matrix interferent;

fractionating the eluted mercury on a cation exchange resin;

obtaining a first fraction comprising organic mercury species;

obtaining a second fraction comprising inorganic mercury species;

quantifying mercury content present in the first fraction; and quantifying mercury content present in the second fraction;

wherein the first fraction is separated from the second fraction; and wherein the first resin comprises thiourea.

27. The method of claim 26, wherein the first fraction comprises at least 98 percent of all organic mercury species in the sample with at most 2 percent contaminating inorganic mercury species, and the second fraction comprises at least 98 percent of all inorganic mercury species in the sample with at most 2 percent contaminating organic mercury species.

28. The method of claim 26, wherein fractionating comprises:
absorbing the sample on the cation exchange resin under conditions that promote retention of inorganic mercury and organic mercury species on the cation exchange resin; and
eluting inorganic mercury and organic mercury species in separate fractions from the cation exchange resin;
wherein the eluting is carried out with an aqueous eluent comprising a bifunctional moiety and a source of protons.

29. The method of claim 28, wherein the aqueous eluent comprises
the bifunctional moiety comprising thiourea having a final concentration in the aqueous eluent in the range from 0.1% (wt/vol) to 10% (wt/vol); and
the source of protons is a dissolved acid having a final concentration in the aqueous eluent of at least 0.1% (wt/vol).

30. The method of claim 26, wherein the quantifying of the mercury content present in the first and second fractions comprises performing at least one analytical method selected from the group consisting of atomic absorption, inductively coupled plasma spectroscopy, inductively coupled plasma-mass spectroscopy, and cold vapor atomic fluorescence spectroscopy.

31. The method of claim 26, further comprising converting the organic mercury species and the inorganic mercury species to elemental mercury.

32. The method of claim 31, further comprising volatilizing the elemental mercury.

33. The method of claim 26, wherein absorbing, eluting, fractionating and quantifying occur in an automated system.

34. A method of performing mercury analysis for a plurality of individual samples, comprising:
loading the individual samples into an autosampler, said autosampler comprising a computer-controlled robotic sampling mechanism that can withdraw each individual sample for analysis; and
performing the method of claim 1 with each individual sample.

35. The method of claim 34, wherein the fractionating of the sample further comprises controlling adsorption and elution of the inorganic and organic mercury species on the cation exchange resin with a computer-operated process.

36. A method of performing mercury analysis for a plurality of samples, comprising:
loading the plurality of samples into an autosampler, said autosampler comprising a computer-controlled robotic sampling mechanism that can withdraw each individual sample for analysis; and
performing the method of claim 26 with each individual sample.

37. The method of claim 36, wherein the fractionating of the eluted mercury further comprises controlling adsorption and elution of the eluted mercury on the cation exchange resin with a computer-operated process.

38. The method of claim 1, wherein the organic mercury species comprises monomethylmercury.

39. The method of claim 9, wherein the organic mercury species comprises monomethylmercury.

40. The method of claim 26, wherein the organic mercury species comprises monomethylmercury.

41. A method of performing mercury analysis for a plurality of individual samples, comprising:
loading the individual samples into an autosampler, said autosampler comprising a computer-controlled robotic sampling mechanism that can withdraw each individual sample for analysis; and
performing the method of claim 9 with each individual sample.

42. The method of claim 41, wherein the fractionating of the sample further comprises controlling adsorption and elution of the inorganic and organic mercury species on the cation exchange resin with a computer-operated process.

43. A method of performing mercury analysis for a plurality of individual samples, comprising:
loading the individual samples into an autosampler, said autosampler comprising a computer-controlled robotic sampling mechanism that can withdraw each individual sample for analysis; and
performing the method of claim 14 with each individual sample.

44. The method of claim 43, wherein the fractionating of the sample further comprises controlling adsorption and elution of the inorganic and organic mercury species on the cation exchange resin with a computer-operated process.

45. The method of claim 14, wherein the organic mercury species comprises monomethylmercury.

46. A method of performing mercury analysis for a plurality of individual samples, comprising:
loading the individual samples into an autosampler, said autosampler comprising a computer-controlled robotic sampling mechanism that can withdraw each individual sample for analysis; and
performing the method of claim 15 with each individual sample.

47. The method of claim 46, wherein the fractionating of the sample further comprises controlling adsorption and elution of the inorganic and organic mercury species on the cation exchange resin with a computer-operated process.

48. The method of claim 15, wherein the organic mercury species comprises monomethylmercury.

49. A method of performing mercury analysis for a plurality of individual samples, comprising:
loading the individual samples into an autosampler, said autosampler comprising a computer-controlled robotic sampling mechanism that can withdraw each individual sample for analysis; and
performing the method of claim 24 with each individual sample.

50. The method of claim 49, wherein the fractionating of the sample further comprises controlling adsorption and elution of the inorganic and organic mercury species on the cation exchange resin with a computer-operated process.

51. The method of claim 24, wherein the organic mercury species comprises monomethylmercury.

* * * * *